US010589127B2

(12) United States Patent
Nord et al.

(10) Patent No.: US 10,589,127 B2
(45) Date of Patent: Mar. 17, 2020

(54) METHOD AND APPARATUS FOR USING PATIENT-EXPERIENCE OUTCOMES WHEN DEVELOPING RADIATION-THERAPY TREATMENT PLANS

(71) Applicant: Varian Medical Systems International AG, Cham (CH)

(72) Inventors: Janne Nord, Espoo (FI); Juha Kauppinen, Espoo (FI); Jarkko Peltola, Tuusula (FI)

(73) Assignee: Varian Medical Systems International AG, Steinhausen (CH)

( * ) Notice: Subject to any disclaimer, the term of this patent is extended or adjusted under 35 U.S.C. 154(b) by 1832 days.

(21) Appl. No.: 14/039,413

(22) Filed: Sep. 27, 2013

(65) Prior Publication Data

US 2014/0275700 A1    Sep. 18, 2014

Related U.S. Application Data

(60) Provisional application No. 61/783,218, filed on Mar. 14, 2013.

(51) Int. Cl.
*A61N 5/10* (2006.01)

(52) U.S. Cl.
CPC ...... *A61N 5/103* (2013.01); *A61N 2005/1041* (2013.01)

(58) Field of Classification Search
CPC .................. A61N 5/103; A61N 5/1038; A61N 2005/1041; A61N 5/1001; A61N 5/1007; A61N 5/1031; A61N 5/1036; A61N 5/1037; A61N 5/1039
See application file for complete search history.

(56) References Cited

U.S. PATENT DOCUMENTS

| 2006/0293583 | A1* | 12/2006 | Saracen | A61N 5/1038 600/407 |
| 2007/0156453 | A1* | 7/2007 | Frielinghaus | A61N 5/103 705/2 |
| 2012/0014507 | A1* | 1/2012 | Wu | A61N 5/10 378/65 |

* cited by examiner

*Primary Examiner* — Carrie R Dorna
(74) *Attorney, Agent, or Firm* — Fitch, Even, Tabin & Flannery LLP

(57) ABSTRACT

A control circuit has access to information that correlates a plurality of patient-experience outcomes with corresponding delivered-radiation metrics and uses that plurality of patient-experience outcomes in conjunction with developing a radiation-therapy treatment plan for a particular patient. Those patient-experience outcomes can comprise, for example, information regarding how various patients fared post-radiation treatment as regards such things as post-radiation treatment life expectancy, tumor eradication success, and one or more other quality-of-life metrics. These teachings will accommodate using a particular one of the patient-experience outcomes as an optimization goal when optimizing candidate radiation-therapy treatment plans to develop the radiation-therapy treatment plan. In such a case these teachings will further accommodate, if desired, permitting a user to modify one or more optimization objectives while displaying intermediate optimization results.

17 Claims, 1 Drawing Sheet

METHOD AND APPARATUS FOR USING PATIENT-EXPERIENCE OUTCOMES WHEN DEVELOPING RADIATION-THERAPY TREATMENT PLANS

RELATED APPLICATION(S)

This application claims the benefit of U.S. Provisional application No. 61/783,218, filed Mar. 14, 2013, which is incorporated by reference in its entirety herein.

TECHNICAL FIELD

This invention relates generally to the therapeutic irradiation of a patient's target volume.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted areas and adjacent healthy tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient. Such treatment plans are often optimized prior to use. (As used herein, "optimization" will be understood to refer to improving upon a candidate treatment plan without necessarily ensuring that the optimized result is, in fact, the singular best solution.) Many optimization approaches use an automated incremental methodology where various optimization results are calculated and tested in turn using a variety of automatically-modified (i.e., "incremented") treatment plan optimization parameters.

Many treatment plans provide for exposing the target volume to radiation from a number of different directions. Arc therapy, for example, comprises one such approach. In such a case it often becomes useful or necessary to also adjust various mechanical components (such as, for example, multi-leaf collimators) of the treatment system when moving the radiation source with respect to the target volume. A radiation-treatment plan therefore often provides information regarding useful or necessary adjustments to various mechanical components of the treatment system during such a treatment.

Treatment plans are typically optimized using the administered dose as the optimization objective and as the measure of the result. In particular, the optimization seeks to assure that a particular specified dose is being uniformly administered through the target volume while avoiding undue dosing of other patient tissues (or, in other cases, that a series of dose histograms that specify acceptable dosing ranges for a variety of locations both in and external to the target volume are met). Such an approach presumes that the specified dose itself is going to be therapeutically effective.

In fact, however, such a presumption may not always prove exactly right, or perhaps more precisely, such a result does not necessarily accord with a patient's expectations or goals. The effect a given dose will have with respect to the patient's bigger picture (i.e., their quality of life and expected longevity, for example) can vary with a variety of anecdotal circumstances such as the patient's age and their ability (and/or willingness) to deal with various side effects, for example.

BRIEF DESCRIPTION OF THE DRAWINGS

The above needs are at least partially met through provision of the method and apparatus for using patient-experience outcomes when developing radiation-therapy treatment plans described in the following detailed description, particularly when studied in conjunction with the drawings, wherein.

Figure 1:
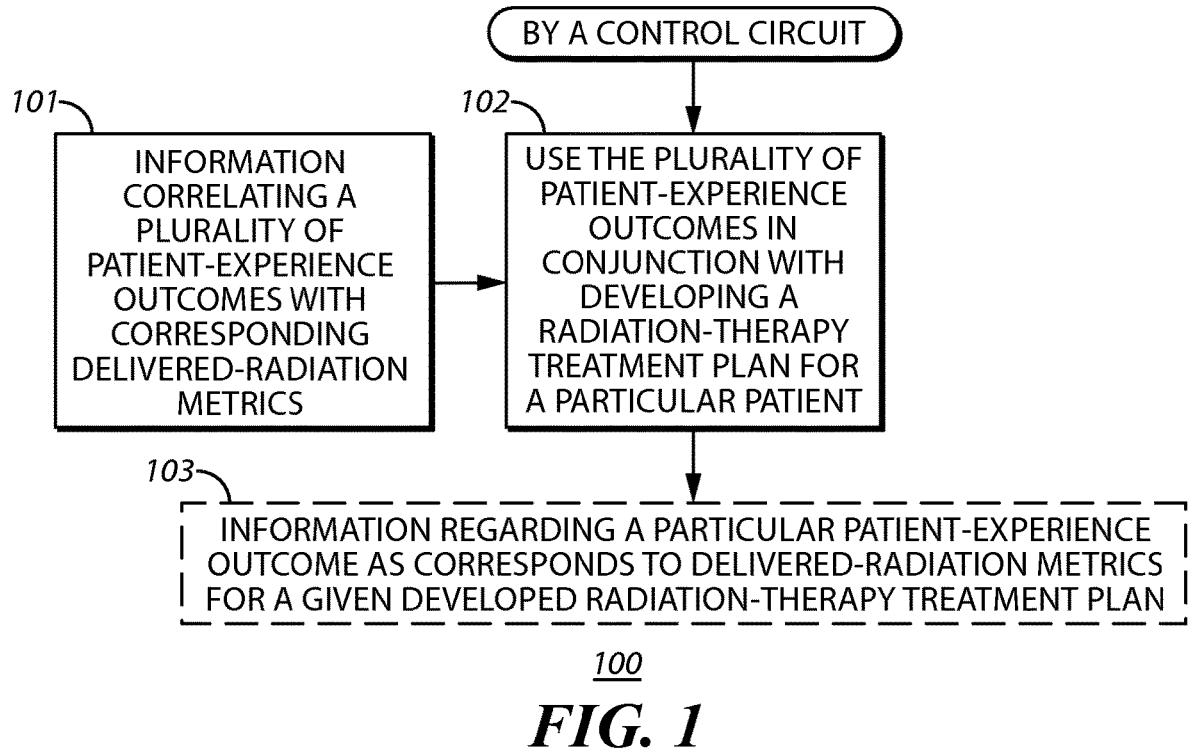
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a control circuit has access to information that correlates a plurality of patient-experience outcomes with corresponding delivered-radiation metrics. That control circuit then uses that plurality of patient-experience outcomes in conjunction with developing a radiation-therapy treatment plan for a particular patient. By one approach that information represents such correlations for a plurality of patients and hence represents a broad population base with respect to those patient-experience outcomes. Those patient-experience outcomes can comprise, for example, information regarding how various patients fared post-radiation treatment as regards such things as post-radiation treatment life expectancy, tumor eradication success, and one or more other quality-of-life experiences (as represented, if desired, via one or more corresponding metrics).

By one approach the foregoing includes providing output information regarding the particular patient-experience outcome to thereby permit a user to take the particular patient-experience outcome into account when evaluating the viability of the developed radiation-therapy treatment plan.

By another approach, in lieu of the foregoing or in combination therewith, these teachings will accommodate using a particular one of the patient-experience outcomes as an optimization goal when optimizing candidate radiation-therapy treatment plans to develop the radiation-therapy treatment plan. In such a case these teachings will further accommodate, if desired, permitting a user to modify one or more optimization objectives while displaying intermediate optimization results.

So configured, these teachings permit, amongst other things, optimizing a radiation-therapy treatment plan as a specific function of one or more patient-experience outcomes. This approach permits the user to optimize a radiation-therapy treatment plan, for example, to particularly favor avoiding one or more specific side effects to thereby accommodate a patient who might prefer a reduced chance of treatment success in favor of a more normal life experience during their remaining lifetime.

These and other benefits may become clearer upon making a thorough review and study of the following detailed description. Referring now to the drawings, and in particular to FIG. 1, an illustrative process 100 that is compatible with many of these teachings will now be presented.

For the sake of an illustrative example it will be presumed here that a control circuit of choice carries out this process. Some examples in these regards are provided further herein.

This process 100 provides access at block 101 to information that correlates a plurality of patient-experience outcomes with corresponding delivered-radiation metrics. For many application settings it will serve well for this plurality of patient-experience outcomes to represent a plurality of patients (i.e., different patients). By one approach it can be useful for these various patients to differ from one another demographically as well as clinically. For example, this plurality of patients can represent a range of ages, races, genders, weights, habits, secondary health considerations, geographic location, and so forth. It can also be useful, if desired, for the aforementioned information to include specific reference to some or all of those patient-characterizing differences.

The aforementioned delivered-radiation metrics can vary with the application setting as desired. By one example these metrics can include, at least in part, radiation-dose distribution information. Radiation-dose distribution information can be characterized and represented in a variety of ways. For example, mean dose and maximum dose information inside a given structure are well known approaches in these regards. Dose-volume histograms may also serve as desired.

Similarly, the aforementioned patient-experience outcomes can be expressed as any one or more of a variety of characterizing expressions or metrics. Generally speaking, patient-experience outcomes include, at least in part, information regarding how patients fare post-radiation treatment in an experiential manner (that is, in a way that the patient can directly perceive). For example, how long did the patient live? What was the patient's quality of life? Did they experience one or more side effects as a result of the radiation treatment? And was the tumor eradiation ultimately viewed as being successful? Some of these outcomes can be represented as a hard metric (for example, the number of months or years that various patients lived following a particular radiation treatment that employed a radiation-therapy treatment plan using particular delivered-radiation metrics). Other outcomes, though perhaps more subjective (such as the patient's perception of their own quality of life), are also nevertheless reasonably cast as a quantified metric. (For example, many health-services caregivers rely on patients to gauge their own pain experience on a scale of one to ten.)

At block 102 the control circuit uses the aforementioned plurality of patient-experience outcomes in conjunction with developing a radiation-therapy treatment plan for a particular patient (who is likely not personally included or otherwise represented in the aforementioned information). Generally the latter can comprise associating information regarding a given patient and the patient-experience outcomes with one or more treatment protocols that each define, at the least and by way of one example, a diagnosis attribute, a staging attribute, a patient age attribute, and a treatment technique attribute.

By one approach the latter comprises using a particular one of the patient-experience outcomes as an optimization goal when optimizing candidate radiation-therapy treatment plans to develop the radiation-therapy treatment plan to actually administer to the patient. Although using a patient-experience outcome as an optimization goal represents a significant variation from past practices as regards optimization (where dosing goals are the more ordinary expectation), such an approach can in fact help specify a radiation-therapy treatment plan that best accords with not only a specific therapeutic intent but the patient's own wishes and expectations as well.

To assist in those regards, and by one optional approach, this process 100 will further accommodate at block 103 optionally providing as an output (via, for example, a corresponding display) information regarding a particular patient-experience outcome as corresponds to the delivered-radiation metrics for a given developed (final or interim) radiation-therapy treatment plan. This information can permit a user (which may comprise the patient and/or a treatment plan medical-services provider or technician) to take the particular patient-experience outcome into account when evaluating suitability of the developed radiation-therapy treatment plan. Such an approach will also accommodate, if desired, permitting the user to modify one or more of the optimization objectives while displaying, for example, intermediate optimization results.

Fundamentally, then, such a process 100 permits patient-experience outcomes to be specifically taken into account when planning a radiation-therapy treatment plan. By one approach this includes using one or more patient-experience outcomes as an optimization objective. Such an approach can permit a patient, for example, to accommodate a willingness to accept an increased chance of a severe side effect in exchange for increasing their likelihood of prolonging their expected lifetime. As another example, another patient can influence their plan to reflect their objective to minimize severe side effects to thereby improve their likely quality of life notwithstanding that their own life expectancy may be less than might otherwise be possible. Put simply, by using patient-experience outcomes as a driver in these ways the patient's own sometimes-subjective hopes for their own circumstances can become an integral part of planning their corresponding treatment.

As a very specific (and overly-simplified example), one radiation-treatment plan that provides for a first dosing of the target volume and a corresponding first dosing of a particular nearby critical organ can be reasonably compared to past plans that had, of record, particular outcomes that, on average, reflect a 95% chance for the patient to live at least another three years and a 65% chance of also developing a particular side effect as a result of collateral harm to that critical organ. And another radiation-treatment plan that provides for a second dosing of the target volume and a corresponding second dosing of that same nearby critical organ can be reasonably compared to past plans that had, of record, particular outcomes that, on average, reflect a 91% chance for the patient to live at least another three years and a 33% chance of also developing that particular side effect. By using outcome-based objectives as inputs to the optimization process these teachings permit the optimization process to aim more for one or the other of these two general outcomes.

Figure 2:
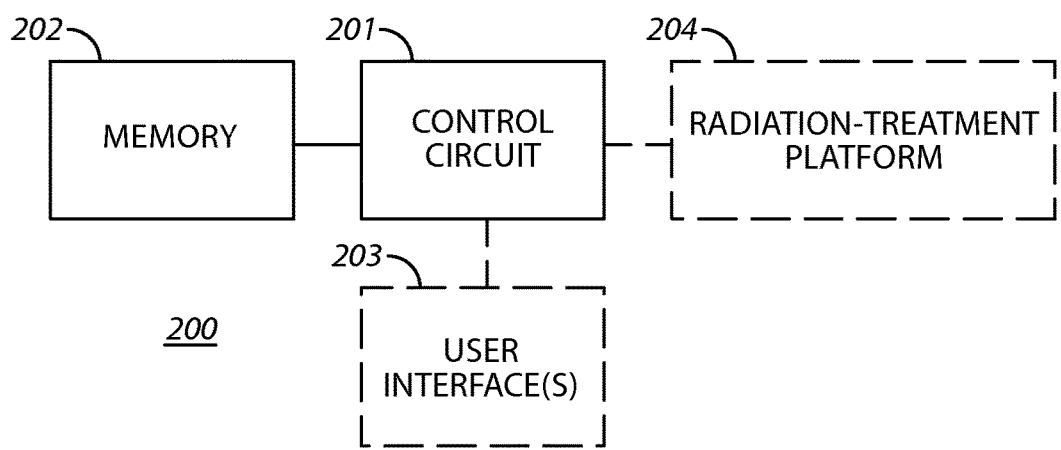
FIG. 2 comprises a block diagram as configured in accordance with various embodiments of the invention.

The above-described processes are readily enabled using any of a wide variety of available and/or readily configured platforms, including partially or wholly programmable platforms as are known in the art or dedicated purpose platforms as may be desired for some applications. Referring now to FIG. 2, an illustrative approach to such a platform 200 will now be provided.

In this example the enabling apparatus 200 includes a control circuit 201 that operably couples to a memory 202 and to an optional user interface 203. Such a control circuit 201 can comprise a fixed-purpose hard-wired platform or can comprise a partially or wholly programmable platform. These architectural options are well known and understood in the art and require no further description here. This control circuit 201 is configured (for example, by using corresponding programming as understood by those skilled in the art) to carry out one or more of the steps, actions, and/or functions described herein.

The memory 202 may be integral to the control circuit 201 or can be physically discrete (in whole or in part) from the control circuit 201 as desired. This memory 202 can also be local with respect to the control circuit 201 (where, for example, both share a common circuit board, chassis, power supply, and/or housing) or can be partially or wholly remote with respect to the control circuit 201 (where, for example, the memory 202 is physically located in another facility, metropolitan area, or even country as compared to the control circuit 201).

This memory 202 can serve, for example, to non-transitorily store the computer instructions that, when executed by the control circuit 201, cause the control circuit 201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

The user interface 203 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

These teachings will also accommodate operably coupling the control circuit 201 to a radiation-treatment platform 204 (such as, by way of a non-limiting illustrative example, an arc-therapy radiation-treatment platform) of choice. So configured, the control circuit 201 can delivered the optimized radiation-therapy treatment plan to that platform 204 for use in treating the corresponding patient.

Such an apparatus 200 may be comprised of a plurality of physically distinct elements as is suggested by the illustration shown in FIG. 2. It is also possible, however, to view this illustration as comprising a logical view, in which case one or more of these elements can be enabled and realized via a shared platform. It will also be understood that such a shared platform may comprise a wholly or at least partially programmable platform as are known in the art.

So configured, these teachings facilitate formulating radiation-therapy treatment plans in a manner that more clearly, directly, and integrally ties the development of the plans to given patient-experience outcomes rather than mere metrics regarding quantities of delivered radiation. Such an approach, in turn, can greatly improve the ability of the patient to participate meaningfully in defining the scope and goals of their own treatment.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An apparatus comprising:
a memory having information stored therein correlating a plurality of patient-experience outcomes with corresponding delivered-radiation metrics;
a control circuit operably coupled to the memory and configured to use the plurality of patient-experience outcomes in conjunction with developing a radiation-therapy treatment plan for a particular patient by, at least in part, using a particular one of the patient-experience outcomes as an optimization goal when optimizing at least one candidate radiation-therapy treatment plan by automatically modifying treatment plan parameters while using an automated incremental methodology where various optimization results are incrementally calculated and tested against the optimization goal to develop the radiation-therapy treatment plan, such that the radiation-therapy treatment plan is optimized as a specific function of the particular one of the patient-experience outcomes; and
a radiation-treatment platform configured to receive the radiation-therapy treatment plan and to use the radiation-therapy treatment plan to treat a corresponding patient.

2. The apparatus of claim 1 wherein the information stored in the memory correlates the plurality of patient-experience outcomes with corresponding delivered-radiation metrics for a plurality of patients.

3. The apparatus of claim 1 wherein the control circuit is configured to use the plurality of patient-experience outcomes in conjunction with developing a radiation-therapy treatment plan for a particular patient by, at least in part, providing as an output information regarding a particular patient-experience outcome as corresponds to delivered-radiation metrics for a given developed radiation-therapy treatment plan to thereby permit a user to take the particular patient-experience outcome into account when evaluating viability of the developed radiation-therapy treatment plan.

4. The apparatus of claim 1 wherein optimizing candidate radiation-therapy treatment plans to develop the radiation-therapy treatment plan comprises, at least in part, permitting a user to modify optimization objectives while displaying intermediate optimization results.

5. The apparatus of claim 1 wherein the delivered-radiation metrics include, at least in part, radiation-dose distribution information.

6. The apparatus of claim 1 wherein the plurality of patient-experience outcomes include, at least in part, information regarding how patients fare post-radiation treatment.

7. The apparatus of claim 6 wherein the information regarding how patients fare post-radiation treatment includes at least one of:
post-radiation treatment life expectancy;

at least one quality-of-life metric; and
tumor eradication success.

8. The apparatus of claim 1 wherein:
the plurality of patient-experience outcomes include, at least in part, information regarding how patients fare post-radiation treatment; and
the information regarding how patients fare post-radiation treatment includes at least one of:
post-radiation treatment life expectancy;
at least one quality-of-life metric; and
tumor eradication success.

9. The apparatus of claim 1 wherein the control circuit is configured to use the plurality of patient-experience outcomes in conjunction with developing a radiation-therapy treatment plan for a particular patient by, at least in part, associating information regarding a patient and the patient-experience outcomes with treatment protocols.

10. The apparatus of claim 9 wherein the treatment protocols define, at the least, a diagnosis attribute, a staging attribute, a patient age attribute, and a treatment technique attribute.

11. A method comprising:
by a control circuit operably coupled to a memory having information stored therein correlating a plurality of patient-experience outcomes with corresponding delivered-radiation metrics:
using the plurality of patient-experience outcomes in conjunction with developing a radiation-therapy treatment plan for a particular patient by, at least in part, using a particular one of the patient-experience outcomes as an optimization goal when optimizing at least one candidate radiation-therapy treatment plan by automatically modifying treatment plan parameters while using an automated incremental methodology where various optimization results are incrementally calculated and tested against the optimization goal to develop the radiation-therapy treatment plan, such that the radiation-therapy treatment plan is optimized as a specific function of the particular one of the patient-experience outcomes; and
using a radiation-treatment platform to receive the radiation-therapy treatment plan and to use the radiation-therapy treatment plan to treat a corresponding patient.

12. The method of claim 11 wherein the information stored in the memory correlates the plurality of patient-experience outcomes with corresponding delivered-radiation metrics for a plurality of patients.

13. The method of claim 11 wherein using the plurality of patient-experience outcomes in conjunction with developing a radiation-therapy treatment plan for a particular patient comprises, at least in part, providing as an output information regarding a particular patient-experience outcome as corresponds to delivered-radiation metrics for a given developed radiation-therapy treatment plan to thereby permit a user to take the particular patient-experience outcome into account when evaluating viability of the developed radiation-therapy treatment plan.

14. The method of claim 11 wherein the delivered-radiation metrics include, at least in part, radiation-dose distribution information.

15. The method of claim 11 wherein the plurality of patient-experience outcomes include, at least in part, information regarding how patients fare post-radiation treatment.

16. The method of claim 15 wherein the information regarding how patients fare post-radiation treatment includes at least one of:
post-radiation treatment life expectancy;
at least one quality-of-life metric; and
tumor eradication success.

17. The method of claim 11 wherein:
the plurality of patient-experience outcomes include, at least in part, information regarding how patients fare post-radiation treatment; and
the information regarding how patients fare post-radiation treatment includes at least one of:
post-radiation treatment life expectancy;
at least one quality-of-life metric; and
tumor eradication success.

* * * * *